(12) United States Patent
Boschat et al.

(10) Patent No.: US 6,521,779 B1
(45) Date of Patent: Feb. 18, 2003

(54) HEMIHYDROGENATION METHOD FOR DINITRILES

(75) Inventors: Vincent Boschat, Lyons (FR); Jean-Pierre Brunelle, Croissy sur Seine (FR); Bernard Darrier, Saucats (FR); Bernard Chevaljer, Talence (FR); Jean Louis Bobet, Pessac (FR)

(73) Assignee: Rhodia Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/831,148
(22) PCT Filed: Nov. 3, 1999
(86) PCT No.: PCT/FR99/02677
§ 371 (c)(1), (2), (4) Date: Sep. 25, 2001
(87) PCT Pub. No.: WO00/27806
PCT Pub. Date: May 18, 2000

(30) Foreign Application Priority Data

Nov. 5, 1998 (FR) .............................................. 98 14100

(51) Int. Cl.[7] .......................................... C07C 255/24
(52) U.S. Cl. ...................................... 558/459; 558/452
(58) Field of Search ................................. 558/459, 452

(56) References Cited

U.S. PATENT DOCUMENTS

| | | | | |
|---|---|---|---|---|
| 4,313,018 A | * | 1/1982 | Holy et al. ................. | 585/269 |
| 4,601,859 A | * | 7/1986 | Galle et al. ................. | 558/459 |
| 5,527,946 A | * | 6/1996 | Flick et al. ................. | 558/459 |
| 6,232,488 B1 | * | 5/2001 | Boschat et al. ............. | 558/459 |

FOREIGN PATENT DOCUMENTS

| | | |
|---|---|---|
| WO | 93 12073 | 6/1993 |
| WO | 93 16034 | 8/1993 |
| WO | 96 18603 | 6/1996 |
| WO | 96 20166 | 7/1996 |

* cited by examiner

Primary Examiner—Joseph K. McKane
Assistant Examiner—Kamal Saeed
(74) Attorney, Agent, or Firm—Burns, Doane, Swecker & Mathis, L.L.P.

(57) ABSTRACT

The invention concerns the hydrogenation in amine function of a nitrile function of a dinitrile to obtain the corresponding aminonitrile. More precisely, the invention concerns the hemihydrogenation of a dinitrile into the corresponding aminonitrile, in a liquid medium, characterized in that it consists in operating in the presence of a Raney nickel or cobalt catalyst containing copper and/or silver and/or gold and in the presence of an alkaline or alkaline-earth metal hydroxide. The hemihydrogenation of adiponitrile provides amino-6 capronitrile, compound which can be easily transformed by cyclization hydrolysis into caprolactam, the starting product for the synthesis of polyamide-6.

20 Claims, No Drawings

HEMIHYDROGENATION METHOD FOR DINITRILES

This application is a 371 of PCT/FR99/02 677 filed Nov. 03, 1999.

The present invention relates to the hydrogenation of a nitrile function of a dinitrile in order to obtain the corresponding aminonitrile.

Generally, the hydrogenation of dinitriles is carried out in order to prepare the corresponding diamines; thus, in particular, the hydrogenation of adiponitrile gives hexamethylenediamine, which is one of the two base compounds in the preparation of nylon-6,6.

However, it occasionally proves to be necessary to prepare not the diamine, but the intermediate aminonitrile. This is the case, for example, but not exclusively, for the hemihydrogenation of adiponitrile into aminocapronitrile, a compound which can then be converted into caprolactam, which is a base material for nylon-6, or directly into nylon-6.

Thus, U.S. Pat. No. 4,389,348 describes a process for the hydrogenation of dinitrile into ω-aminonitrile, with hydrogen, in an aprotic solvent medium and ammonia and in the presence of rhodium deposited on a basic support.

U.S. Pat. No. 5,151,543 describes a process for the partial hydrogenation of dinitriles into aminonitriles in a solvent in a molar excess of at least 2/1 relative to the dinitrile, comprising liquid ammonia or an alkanol containing an inorganic base which is soluble in the said alkanol, in the presence of a catalyst of Raney nickel or cobalt type.

Patent application WO-A-96/18603 describes a process for the hemihydrogenation of aliphatic dinitriles into the corresponding aminonitriles, using hydrogen and in the presence of a catalyst chosen from Raney nickel and Raney cobalt, the said Raney nickel or cobalt preferably comprising a doping element such as chromium, iron, titanium or zinc, and a strong inorganic base derived from an alkali metal or alkaline-earth metal, the initial hydrogenation medium comprising water in a proportion of at least 0.5% by weight relative to the total amount of liquid compounds in the said medium, diamine and/or aminonitrile which are capable of being formed from the dinitrile to be hydrogenated, as well as unconverted dinitrile in a proportion for these three compounds together of from 80% to 99.5% by weight relative to the total amount of liquid compounds in the said medium.

As emerges from the preceding analysis, processes for the hemihydrogenation of dinitriles into aminonitriles usually use a catalyst of Raney nickel or cobalt type, preferably doped by the presence of one or more other elements.

It has now been found that the presence of copper and/or silver and/or gold in Raney nickel or cobalt gives, unexpectedly, excellent results in terms of selectivity towards aminonitrile.

The selective hydrogenation of a single nitrile function of a dinitrile is by nature very difficult to achieve, since the aminonitrile is the intermediate compound in the complete hydrogenation to diamine. This intermediate thus enters into competition with the starting dinitrile as a compound capable of being hydrogenated. Consequently, the overall distribution between aminonitrile and diamine obtained results from the ratio of the kinetic coefficients of hydrogenation of the first nitrile function (k1) and of the second nitrile function (k2).

It has been found that the use of a Raney cobalt or nickel doped with at least one metal chosen from copper, silver and gold makes it possible to improve the k1/k2 ratio of these kinetic coefficients and thus the selectivity of the hydrogenation towards aminonitrile relative to the complete hydrogenation into diamine, in comparison with the use of a Raney catalyst doped with the elements most commonly used, such as, for example, chromium, iron or titanium.

The present invention relates to the preferential hydrogenation of only one nitrile function of a dinitrile (also referred to in the present text as hemihydrogenation) so as to prepare the corresponding aminonitrile predominantly and the diamine only to a minor extent.

More specifically, the invention relates to a process for the hemihydrogenation of a dinitrile into the corresponding aminonitrile, in a liquid medium, characterized in that the process is performed in the presence of a Raney nickel or cobalt catalyst containing at least one metal chosen from copper, silver and gold and in the presence of an alkali metal or alkaline-earth metal hydroxide.

Raney nickels are catalysts that are widely used in the industry for hydrogenation reactions. They are prepared by alkaline attack of aluminium-rich Al/Ni or Al/Co alloys possibly containing other metals, which are generally referred to as doping agents or promoters. The catalyst consists of aggregations of nickel or cobalt crystallites with a large specific surface area and a variable residual aluminium concentration.

This catalyst generally comprises an aluminium content, expressed by weight relative to the weight of the nickel or cobalt, of less than or equal to 10%.

Advantageously, the (Cu+Ag+Au)/Ni or (Cu+Ag+Au)/Co weight ratio of the catalyst used in the present invention is between 0.05% and 10% and preferably between 0.1% and 5%.

Along with copper and/or silver and/or gold, the catalyst used in the process can contain amounts, generally smaller amounts, of one or more other elements also included under the generic term of doping agent or promoter.

These additional doping-agents which may be present are preferably chosen from the following elements: titanium, chromium, iron, zirconium, vanadium, manganese, bismuth, tantalum, rhodium, ruthenium, iridium, platinum, palladium, niobium, hafnium and rare-earth elements. When the catalyst used is Raney nickel, cobalt can also be present as an additional doping agent.

Similarly, when the catalyst used is Raney cobalt, nickel can also be present as an additional doping agent. Titanium, chromium, iron and zirconium are particularly preferred.

The amount of doping agent other than copper, silver and gold which the catalyst can contain generally represents from 0% to 5% by weight relative to the weight of the nickel or cobalt.

Among the catalysts of Raney type used, Raney nickel as defined above will be preferred.

The catalyst used in the present invention can also be used in the form of grains.

The process of the invention applies more particularly, but not exclusively, to the dinitrile substrates of formula (I):

$$NC-R-CN \qquad (I)$$

in which R represents a linear or branched alkylene group containing from 1 to 12 carbon atoms.

Preferably, in the process of the invention, dinitriles of formula (I) are used in which R represents a linear or branched alkylene radical containing from 1 to 6 carbon atoms.

Examples of such dinitriles which may be mentioned in particular are adiponitrile, methylglutaronitrile, ethylsuccinonitrile, malononitrile, succinonitrile and glutaronitrile as well as mixtures of several of these dinitriles, in particular the adiponitrile, methylglutaronitrile and ethylsuccinonitrile mixtures derived from the same process for the synthesis of adiponitrile.

The concentration of dinitriles, in particular of adiponitrile, in the reaction medium can vary widely depending on the embodiment of the invention, continuous or batchwise operation, the initial load or gradual introduction, for example. In the preferred context of an industrial process operating continuously, the average dinitrile concentration is usually between 10% and 45% on a weight for weight basis.

The alkali metal hydroxides, LiOH, NaOH, KOH, RbOH and CsOH, and mixtures thereof, are preferably used.

In practice, NaOH and KOH are preferably used for a good performance-price compromise.

The hydrogenation reaction medium is liquid. It contains at least one solvent capable of at least partially dissolving the dinitrile substrate to be hydrogenated.

According to one advantageous embodiment of the process according to the invention, a liquid reaction medium which is at least partially aqueous is used. The water generally represents an amount of from 1% to 25% by weight relative to the total weight of the reaction medium. Preferably, the water content of the reaction medium is between 1 and 15% on a weight for weight basis.

At least one other solvent, generally of alcohol type, may be provided in addition to or in replacement for the water. The alcohols which are more particularly suitable are, for example, methanol, ethanol, propanol, isopropanol and butanol, and mixtures of the said compounds.

When it is used with water, the alcoholic solvent represents from two to four parts by weight per one part by weight of water and preferably three parts per one part of water.

According to another preferred characteristic of the invention, the initial hydrogenation medium comprises, in particular in the context of a continuous implementation of the process, diamine which is co-produced by the hydrogenation. An example is hexamethylenediamine, when the dinitrile substrate is adiponitrile.

The average concentration of aminonitrile and/or of diamine in the reaction medium under continuous operating conditions is advantageously between 35% and 90% by weight relative to the total weight of the solvent included in the said reaction medium, and is more preferably between 45% and 89% on a weight for weight basis.

The reaction medium can comprise liquid or dissolved ammonia. The ammonia generally represents from 0% to 50% of the weight of the reaction medium and preferably from 0% to 15%.

The amount of alkali metal or alkaline-earth metal hydroxide in the reaction medium varies depending on the nature of the said reaction medium.

Once the reaction medium contains only water, the reaction products and optionally ammonia, as liquid solvent medium, the amount of alkali metal or alkaline-earth metal hydroxide is advantageously greater than or equal to 0.1 mol/kg of catalyst, preferably between 0.1 and 2 mol/kg of catalyst and even more preferably between 0.2 and 1.0 mol/kg of catalyst.

When the reaction medium also comprises an alcohol, the amount of alkali metal or alkaline-earth metal hydroxide is greater than or equal to 0.05 mol/kg of catalyst, preferably between 0.1 and 10.0 mol/kg and even more preferably between 1.0 and 8.0 mol/kg.

The temperature at which the hemihydrogenation process is carried out is generally less than or equal to 150° C., preferably less than or equal to 120° C. and even more preferably less than or equal to 100° C.

In practical terms, this temperature is usually between room temperature (about 20° C.) and 100° C.

Before, during or after heating, the reaction chamber is brought to a suitable hydrogen pressure, i.e., in practice, between 0.10 and 10 MPa.

The reaction time is variable depending on the reaction conditions and the catalyst.

In a batchwise operating mode, it can range from a few minutes to a few hours.

In a continuous operating mode, which is preferred for the process according to the invention, the reaction time is obviously not a fixable parameter.

It should be noted that a person skilled in the art can modify the chronology of the steps in the process according to the invention depending on the operating conditions. The order given above merely corresponds to one preferred, but not limiting, embodiment of the process according to the invention.

The other conditions which govern the hydrogenation (in continuous or batchwise mode) in accordance with the invention concern conventional technical arrangements which are known per se.

By means of all the advantageous arrangements mentioned above, the process of the invention makes it possible to hydrogenate dinitrile substrates into the corresponding aminonitriles, selectively, quickly, conveniently and economically.

The hemihydrogenation of adiponitrile gives 6-aminocapronitrile, a compound which can be readily converted by cyclizing hydrolysis into caprolactam, which is a starting material in the synthesis of nylon-6.

The invention is illustrated by the examples which follow, of the hemihydrogenation of adiponitrile into 6-aminocapronitrile.

In these examples, the following abbreviations may be used:

ADN=adiponitrile

ACN=aminocapronitrile

HMD=hexamethylenediamine

ACA=aminocaproamide

CVA=cyanovaleramide

DC=degree of conversion

RC=selectivity relative to the starting substrate converted (in this case relative to the ADN)

RY=yield relative to the starting substrate (ADN) used

IPOL=polarographic index reflecting the presence of impurities, in particular of imine type, which bring about in particular colorations and branching during polymerization of caprolactam (prepared by hydrolysis of ACN), if they are found in the latter material; this polarographic index is thus determined by polarography and is expressed as moles of imine function per metric ton of sample to be assayed.

EXAMPLE 1

The following are loaded into a 100 ml stainless steel reactor fitted with a stirrer of rushtone cavitator type, means for introducing the reagents and hydrogen and a temperature regulation system:

| | |
|---|---|
| adiponitrile | 24.0 g |
| hexamethylenediamine | 24.0 g |

-continued

| | |
|---|---|
| water | 5.3 g |
| KOH | 0.064 g |
| Raney Ni (containing 1.7% Cu) | 1.35 g |

After purging the reactor with nitrogen and then with hydrogen, the reaction mixture is heated to 50° C. The pressure is then adjusted to 2.5 MPa at this temperature by continuous addition of hydrogen. The reaction progress is monitored by means of the consumption of hydrogen and analysis by gas chromatography (GC) of a sample of the reaction mixture. When the optimum yield is reached, the reaction is stopped by stopping the stirring and cooling the reaction mixture.

The following results are obtained:

| | |
|---|---|
| reaction time: | 321 min |
| DC of the ADN: | 82.3% |
| RY of ACN: | 60.3% |
| RY of HMD: | 20.9% |
| sum of the RCs in respect of ACN and HMD: | 98.7% |
| IPOL index: | 15.0 |

The remainder to 100% of the RCs and of the compounds evaluated by the IPOL index is represented by ACA and CVA, which are compounds that can be upgraded during the cyclizlng hydrolysis of ACN into caprolactam.

EXAMPLE 2

Example 1 is repeated in the same apparatus, with the same amounts of reagents and under the same conditions, but using Raney Ni comprising 3% by weight of Cu.

The following results are obtained:

| | |
|---|---|
| reaction time: | 395 min |
| DC of the ADN: | 85.7% |
| RY of ACN: | 58.9% |
| RY of HMD: | 21.0% |
| sum of the RCs in respect of ACN and HMD: | 93.2% |
| IPOL index: | 19.6 |

The remainder to 100% of the RCs and of the compounds evaluated by the IPOL index is represented by ACA and CVA.

EXAMPLE 3

Example 1 is repeated in the same apparatus, with the same amounts of reagents and under the same conditions, but using Raney Ni comprising 3% by weight of copper and 2.1% by weight of chromium.

The following results are obtained:

| | |
|---|---|
| reaction time | 29 min |
| DC of the ADN | 80.3% |
| RY of the ACN | 56.3% |
| RY of the HMD | 24.5% |

-continued

| | |
|---|---|
| sum of the RCs in respect of ACN and HMD | 100% |
| IPOL index | 26 |

Comparative Test 1

Example 1 is repeated in the same apparatus, with the same amounts of reagents and under the same conditions, but using Raney Ni comprising 1.7% by weight of chromium.

The following results are obtained:

| | |
|---|---|
| reaction time: | 30 min |
| DC of the ADN: | 81.7% |
| RY of the ACN: | 56.9% |
| RY of the HMD: | 22.4% |
| sum of the RCs in respect of ACN and HMD: | 97.1% |
| IPOL index: | 72.5 |

The remainder to 100% of the RCs and of the compounds evaluated by the IPOL index is represented by side products not taken into account in the IPOL index and other than ACA and CVA (for example bis-hexamethylenetriamine).

What is claimed is:

1. Process for the hemihydrogenation of a dinitrile into the corresponding aminonitrile, in a liquid medium, wherein the process is performed in the presence of a Raney nickel or cobalt catalyst containing at least one metal selected from the group consisting of copper, silver and gold and in the presence of an alkali metal or alkaline-earth metal hydroxide.

2. Process according to claim 1, wherein the (Cu+Ag+Au)/Ni or (Cu+Ag+Au)/Co weight ratio of the catalyst used is between 0.05% and 10%.

3. Process according to claim 1, wherein the catalyst contains one or more additional doping agents selected from the group consisting of titanium, chromium, iron, zirconium, vanadium, manganese, bismuth, tantalum, rhodium, ruthenium, iridium, platinum, palladium, niobium, hafnium and rare-earth elements, as well as cobalt when the catalyst is Raney nickel and nickel when the catalyst is Raney cobalt.

4. Process according to claim 1, wherein the amount of doping agent other than copper, silver and gold which the catalyst contains represents from 0% to 5% by weight relative to the weight of the nickel or cobalt.

5. Process according to claim 1, wherein the catalyst used is Raney nickel.

6. Process according to claim 1, wherein the catalyst is in the form of grains.

7. Process according to claim 1, which applies to the dinitrile substrates of formula (I):

NC—R—CN          (I)

in which R represents a linear or branched alkylene group containing from 1 to 12 carbon atoms.

8. Process according to claim 1, wherein the average concentration of dinitrile in the reaction medium in the context of an industrial process operating continuously is between 10% and 45% on a weight for weight basis.

9. Process according to claim 1, which is carried out in the presence of LiOH, NaOH, KOH, RbOH or CsOH, and mixtures thereof.

10. Process according to claim 1, wherein the liquid reaction medium is at least partially aqueous and the water represents an amount of from 1% to 25% by weight relative to the total weight of the reaction medium.

11. Process according to claim 1, wherein the reaction medium comprises at least one other solvent of alcohol type in addition to or in replacement for the water.

12. Process according to claim 11, wherein the reaction medium comprises an alcohol selected from the group consisting of methanol, ethanol, propanol, isopropanol and butanol, and mixtures of the said compounds.

13. Process according to claim 1, wherein the reaction medium comprises diamine which is co-produced by the hydrogenation.

14. Process according to claim 13, wherein the average concentration of aminonitrile and/or of diamine in the reaction medium under continuous operating conditions is between 35% and 90% by weight relative to the total weight of the solvent included in the said reaction medium.

15. Process according to claim 1, wherein the reaction medium comprises liquid or dissolved ammonia.

16. Process according to claim 1, wherein the ammonia represents from 0% to 50% of the weight of the reaction medium.

17. Process according to claim 1, wherein the amount of alkali metal or alkaline-earth metal hydroxide is greater than or equal to 0.1 mol/kg of catalyst.

18. Process according to claim 1, wherein the amount of alkali metal or alkaline-earth metal hydroxide is greater than or equal to 0.05 mol/kg of catalyst.

19. Process according to claim 1, which is carried out at a temperature of less than or equal to 150° C.

20. Process according to claim 1, which is carried out under a hydrogen pressure of between 0.10 and 10 MPa.

* * * * *